(12) United States Patent
Scott et al.

(10) Patent No.: US 7,881,796 B2
(45) Date of Patent: Feb. 1, 2011

(54) IMPLANTABLE MEDICAL DEVICE WITH A NONHERMETIC BATTERY

(75) Inventors: Erik R. Scott, Maple Grove, MN (US); Carl D. Wahlstrand, Lino Lakes, MN (US); Robert M. Skime, Coon Rapids, MN (US); Craig L. Schmidt, Eagan, MN (US)

(73) Assignee: Medtronic, Inc., Minneapolis, MN (US)

( * ) Notice: Subject to any disclaimer, the term of this patent is extended or adjusted under 35 U.S.C. 154(b) by 10 days.

(21) Appl. No.: 11/831,333

(22) Filed: Jul. 31, 2007

(65) Prior Publication Data
US 2008/0021511 A1 Jan. 24, 2008

Related U.S. Application Data

(62) Division of application No. 10/835,233, filed on Apr. 29, 2004, now Pat. No. 7,263,401.

(60) Provisional application No. 60/471,262, filed on May 16, 2003.

(51) Int. Cl.
*A61N 1/08* (2006.01)

(52) U.S. Cl. .............................. 607/36; 607/37; 607/63

(58) Field of Classification Search ................. 607/36, 607/37, 63, 116, 119; 174/50.5; 257/682; 200/216; 52/140
See application file for complete search history.

(56) References Cited

U.S. PATENT DOCUMENTS

| 3,310,051 A | 3/1967 | Schulte |
| 3,522,811 A | 8/1970 | Schwartz et al. |
| 3,690,325 A | 9/1972 | Kenny |
| 3,724,467 A | 4/1973 | Avery et al. |

(Continued)

FOREIGN PATENT DOCUMENTS

| DE | 3940632 | 12/1990 |

(Continued)

OTHER PUBLICATIONS

Notification of Transmittal of the International Search Report and the Written Opinion of the International Searching Authority, International Application No. PCT/US2004/014804, flied May 12, 2004.

(Continued)

*Primary Examiner*—Carl H Layno
*Assistant Examiner*—Natasha N Patel
(74) *Attorney, Agent, or Firm*—Shumaker & Sieffert, P.A.

(57) ABSTRACT

An implantable medical device (IMD) including a nonhermetic battery is described. The IMD includes components and a power source module that includes the nonhermetic battery. The IMD also includes a barrier to substantially impede movement of substances from the nonhermetic battery to the components. The barrier may include a hermetic feedthrough, a gel, a polymer, or a solid electrolyte within the nonhermetic battery, and a seal member. The barrier may also be a material that encapsulates the nonhermetic battery and a getter within the IMD. In some embodiments, the IMD comprises a modular IMD including an interconnect member. In that case, the barrier may include a material that fills at least a portion of a void defined by the interconnect member. A length and a cross-sectional area of the interconnect member may also act as a barrier.

20 Claims, 8 Drawing Sheets

U.S. PATENT DOCUMENTS

| | | | |
|---|---|---|---|
| 3,888,260 A | 6/1975 | Fischell | |
| 3,913,587 A | 10/1975 | Newash | |
| 3,941,135 A | 3/1976 | von Sturm et al. | |
| 4,006,748 A * | 2/1977 | Schulman | 607/36 |
| 4,010,760 A | 3/1977 | Kraska et al. | |
| 4,013,081 A | 3/1977 | Kolenik | |
| 4,040,412 A | 8/1977 | Sato | |
| 4,266,552 A | 5/1981 | Dutcher et al. | |
| 4,328,813 A | 5/1982 | Ray | |
| 4,399,819 A | 8/1983 | Cowdery | |
| 4,399,820 A | 8/1983 | Wirtzfeld et al. | |
| 4,616,655 A | 10/1986 | Weinberg et al. | |
| 4,911,178 A | 3/1990 | Neal | |
| 4,928,696 A | 5/1990 | Henderson et al. | |
| 4,969,899 A | 11/1990 | Cox, Jr. | |
| 5,085,644 A | 2/1992 | Watson et al. | |
| 5,116,345 A | 5/1992 | Jewell et al. | |
| 5,144,946 A | 9/1992 | Weinberg et al. | |
| 5,197,332 A | 3/1993 | Shennib | |
| 5,207,218 A | 5/1993 | Carpentier et al. | |
| 5,218,959 A | 6/1993 | Fenster | |
| 5,220,929 A | 6/1993 | Marquit | |
| 5,252,090 A | 10/1993 | Giurtino et al. | |
| 5,271,397 A | 12/1993 | Seligman et al. | |
| 5,312,440 A | 5/1994 | Hirschberg et al. | |
| 5,314,451 A | 5/1994 | Mulier | |
| 5,314,453 A | 5/1994 | Jeutter | |
| 5,411,537 A | 5/1995 | Munshi et al. | |
| 5,411,538 A | 5/1995 | Lin | |
| H1465 H | 7/1995 | Stokes | |
| 5,431,695 A | 7/1995 | Wiklund et al. | |
| 5,433,734 A | 7/1995 | Stokes et al. | |
| 5,455,999 A | 10/1995 | Owens et al. | |
| 5,458,997 A | 10/1995 | Crespi et al. | |
| 5,477,855 A | 12/1995 | Schindler et al. | |
| 5,480,416 A | 1/1996 | Garcia et al. | |
| 5,489,225 A | 2/1996 | Julian | |
| 5,554,194 A | 9/1996 | Sanders | |
| 5,562,715 A | 10/1996 | Czura et al. | |
| 5,571,148 A | 11/1996 | Loeb et al. | |
| 5,573,551 A | 11/1996 | Lin et al. | |
| 5,638,832 A | 6/1997 | Singer et al. | |
| 5,645,586 A | 7/1997 | Meltzer | |
| 5,674,260 A | 10/1997 | Weinberg | |
| 5,678,559 A | 10/1997 | Drakulic | |
| 5,702,430 A | 12/1997 | Slimon et al. | |
| 5,741,313 A | 4/1998 | Nason et al. | |
| 5,755,743 A | 5/1998 | Volz et al. | |
| 5,769,874 A | 6/1998 | Dahlberg | |
| 5,773,961 A | 6/1998 | Cameron et al. | |
| 5,776,169 A | 7/1998 | Schroeppel | |
| 5,792,067 A | 8/1998 | Karell | |
| 5,800,535 A | 9/1998 | Howard, III | |
| 5,814,095 A | 9/1998 | Leysieffer et al. | |
| 5,836,935 A | 11/1998 | Ashton et al. | |
| 5,843,150 A | 12/1998 | Adams et al. | |
| RE36,120 E | 3/1999 | Karell | |
| 5,876,424 A | 3/1999 | O'Phelan et al. | |
| 5,895,414 A | 4/1999 | Sanchez-Zambrano | |
| 5,896,647 A | 4/1999 | Shkuratoff | |
| 5,919,215 A | 7/1999 | Haeg et al. | |
| 5,935,154 A | 8/1999 | Westlund | |
| 5,941,905 A | 8/1999 | Single | |
| 5,941,906 A | 8/1999 | Barreras, Sr. et al. | |
| 5,958,088 A | 9/1999 | Vu et al. | |
| 5,984,859 A | 11/1999 | Lesinski | |
| 5,991,664 A | 11/1999 | Seligman | |
| 6,006,124 A | 12/1999 | Fischell et al. | |
| 6,016,449 A | 1/2000 | Fischell et al. | |
| 6,016,593 A | 1/2000 | Kyrstein | |
| 6,044,304 A | 3/2000 | Baudino | |
| 6,061,593 A | 5/2000 | Fischell et al. | |
| 6,067,474 A | 5/2000 | Schulman et al. | |
| 6,091,979 A | 7/2000 | Madsen | |
| 6,112,120 A | 8/2000 | Correas | |
| 6,128,538 A | 10/2000 | Fischell et al. | |
| 6,131,581 A | 10/2000 | Leysieffer et al. | |
| 6,134,474 A | 10/2000 | Fischell et al. | |
| 6,154,677 A | 11/2000 | Leysieffer | |
| 6,162,487 A | 12/2000 | Darouiche | |
| 6,168,580 B1 | 1/2001 | Yardley | |
| 6,176,879 B1 | 1/2001 | Leysieffer et al. | |
| 6,205,358 B1 | 3/2001 | Haeg et al. | |
| 6,214,032 B1 | 4/2001 | Loeb et al. | |
| 6,218,016 B1 | 4/2001 | Tedeschi et al. | |
| 6,230,049 B1 | 5/2001 | Fischell et al. | |
| 6,248,080 B1 | 6/2001 | Miesel et al. | |
| 6,248,126 B1 | 6/2001 | Lesser et al. | |
| 6,259,951 B1 | 7/2001 | Kuzma et al. | |
| 6,263,225 B1 | 7/2001 | Howard, III | |
| 6,266,556 B1 | 7/2001 | Ives et al. | |
| 6,269,266 B1 * | 7/2001 | Leysieffer | 607/2 |
| 6,272,382 B1 | 8/2001 | Lenarz et al. | |
| 6,308,101 B1 | 10/2001 | Gord et al. | |
| 6,324,428 B1 | 11/2001 | Weinberg et al. | |
| 6,324,433 B1 | 11/2001 | Errico | |
| 6,330,468 B1 | 12/2001 | Scharf | |
| 6,354,299 B1 | 3/2002 | Fischell et al. | |
| 6,356,792 B1 | 3/2002 | Zonenshayn et al. | |
| 6,358,281 B1 | 3/2002 | Berrang et al. | |
| 6,360,122 B1 | 3/2002 | Fischell et al. | |
| 6,366,813 B1 | 4/2002 | DiLorenzo | |
| 6,405,079 B1 | 6/2002 | Ansarinia | |
| 6,415,184 B1 | 7/2002 | Ishikawa et al. | |
| 6,427,086 B1 | 7/2002 | Upton et al. | |
| 6,436,422 B1 | 8/2002 | Trogolo et al. | |
| 6,456,256 B1 | 9/2002 | Amundson et al. | |
| 6,456,886 B1 | 9/2002 | Howard et al. | |
| 6,480,743 B1 | 11/2002 | Kirkpatrick et al. | |
| 6,490,486 B1 | 12/2002 | Bradley | |
| 6,498,951 B1 | 12/2002 | Larson et al. | |
| 6,505,077 B1 | 1/2003 | Kast et al. | |
| 6,516,227 B1 | 2/2003 | Meadows et al. | |
| 6,516,808 B2 | 2/2003 | Schulman | |
| 6,517,476 B1 | 2/2003 | Bedoya et al. | |
| 6,537,200 B2 | 3/2003 | Leysieffer et al. | |
| 6,554,762 B2 | 4/2003 | Leysieffer | |
| 6,560,486 B1 | 5/2003 | Frei et al. | |
| 6,565,503 B2 | 5/2003 | Leysieffer et al. | |
| 6,567,703 B1 | 5/2003 | Thompson et al. | |
| 6,575,894 B2 | 6/2003 | Leysieffer et al. | |
| 6,597,954 B1 | 7/2003 | Pless et al. | |
| 6,618,623 B1 | 9/2003 | Pless et al. | |
| 6,626,680 B2 | 9/2003 | Ciurzynski et al. | |
| 6,648,914 B2 | 11/2003 | Berrang et al. | |
| 6,671,544 B2 | 12/2003 | Baudino | |
| 6,726,678 B1 | 4/2004 | Nelson et al. | |
| 6,736,770 B2 | 5/2004 | Leysieffer et al. | |
| 6,788,974 B2 | 9/2004 | Bardy et al. | |
| 6,805,998 B2 | 10/2004 | Jenson et al. | |
| 6,882,881 B1 | 4/2005 | Lesser et al. | |
| 6,899,976 B2 | 5/2005 | Larson et al. | |
| 6,963,780 B2 | 11/2005 | Ruben et al. | |
| 6,977,124 B2 | 12/2005 | Probst et al. | |
| 6,994,933 B1 * | 2/2006 | Bates | 429/162 |
| 7,010,351 B2 | 3/2006 | Firlik et al. | |
| 7,103,415 B2 | 9/2006 | Probst et al. | |
| 7,107,097 B2 | 9/2006 | Stern et al. | |
| 7,110,819 B1 | 9/2006 | O'Hara | |
| 7,212,864 B2 | 5/2007 | Wahlstrand et al. | |
| 7,242,982 B2 | 7/2007 | Singhal et al. | |
| 7,263,401 B2 | 8/2007 | Scott et al. | |
| 7,454,251 B2 | 11/2008 | Rezai et al. | |
| 2001/0033953 A1 | 10/2001 | Takeuchi et al. | |

| | | | |
|---|---|---|---|
| 2001/0051819 A1 | 12/2001 | Fischell et al. | |
| 2002/0002390 A1 | 1/2002 | Fischell et al. | |
| 2002/0013612 A1 | 1/2002 | Whitehurst | |
| 2002/0019669 A1 | 2/2002 | Berrang et al. | |
| 2002/0042634 A1 | 4/2002 | Bardy et al. | |
| 2002/0051550 A1 | 5/2002 | Leysieffer | |
| 2002/0072770 A1 | 6/2002 | Pless | |
| 2002/0077670 A1 | 6/2002 | Archer et al. | |
| 2002/0087201 A1 | 7/2002 | Firlik et al. | |
| 2002/0099412 A1 | 7/2002 | Fischell et al. | |
| 2002/0103510 A1 | 8/2002 | Bardy et al. | |
| 2002/0107546 A1 | 8/2002 | Ostroff et al. | |
| 2002/0161403 A1 | 10/2002 | Meadows et al. | |
| 2002/0165588 A1 | 11/2002 | Fraley et al. | |
| 2002/0169485 A1 | 11/2002 | Pless et al. | |
| 2002/0177882 A1 | 11/2002 | DiLorenzo | |
| 2003/0004428 A1 | 1/2003 | Pless et al. | |
| 2003/0004546 A1 | 1/2003 | Casey | |
| 2003/0017372 A1 | 1/2003 | Probst et al. | |
| 2003/0040781 A1 | 2/2003 | Sunderland et al. | |
| 2003/0073972 A1 | 4/2003 | Rosenman et al. | |
| 2003/0085684 A1 | 5/2003 | Tsukamoto et al. | |
| 2003/0088294 A1 | 5/2003 | Gesotti | |
| 2003/0091893 A1 | 5/2003 | Kishiyama et al. | |
| 2003/0109903 A1 | 6/2003 | Berrang et al. | |
| 2003/0125786 A1 | 7/2003 | Gliner et al. | |
| 2003/0130706 A1 | 7/2003 | Sheffield et al. | |
| 2003/0171787 A1 | 9/2003 | Money et al. | |
| 2003/0204229 A1 | 10/2003 | Stokes | |
| 2004/0082977 A1 | 4/2004 | Engmark et al. | |
| 2004/0102828 A1 | 5/2004 | Lowry et al. | |
| 2004/0172090 A1 | 9/2004 | Janzig et al. | |
| 2004/0173221 A1 | 9/2004 | Singhal et al. | |
| 2004/0176673 A1 | 9/2004 | Wahlstrand et al. | |
| 2004/0176750 A1 | 9/2004 | Nelson et al. | |
| 2004/0176814 A1 | 9/2004 | Singhal et al. | |
| 2004/0176815 A1 | 9/2004 | Janzig et al. | |
| 2004/0176816 A1 | 9/2004 | Singhal et al. | |
| 2004/0176818 A1 | 9/2004 | Wahlstrand et al. | |
| 2004/0176819 A1 | 9/2004 | Wahlstrand et al. | |
| 2004/0181263 A1 | 9/2004 | Balzer et al. | |
| 2004/0186528 A1 | 9/2004 | Ries et al. | |
| 2005/0003268 A1 | 1/2005 | Scott et al. | |
| 2005/0004619 A1 | 1/2005 | Wahlstrand et al. | |
| 2005/0004620 A1 | 1/2005 | Singhal et al. | |
| 2005/0004637 A1 | 1/2005 | Singhal et al. | |
| 2005/0033378 A1 | 2/2005 | Sheffield et al. | |
| 2005/0070971 A1 | 3/2005 | Fowler et al. | |
| 2005/0075679 A1 | 4/2005 | Gliner et al. | |
| 2005/0245806 A1 | 11/2005 | Singhal et al. | |
| 2005/0245984 A1 | 11/2005 | Singhal et al. | |
| 2006/0116743 A1 | 6/2006 | Gibson et al. | |
| 2006/0129205 A1 | 6/2006 | Boveja et al. | |
| 2006/0149336 A1 | 7/2006 | Meadows | |
| 2006/0184210 A1 | 8/2006 | Singhal et al. | |
| 2006/0184220 A1 | 8/2006 | Singhal et al. | |
| 2006/0195156 A1 | 8/2006 | Singhal et al. | |
| 2007/0074732 A1 | 4/2007 | Singhal et al. | |
| 2007/0185539 A1 | 8/2007 | Singhal et al. | |
| 2007/0255338 A1 | 11/2007 | Wahlstrand | |

FOREIGN PATENT DOCUMENTS

| | | |
|---|---|---|
| DE | 19837912 C1 | 10/1999 |
| EP | 1 145 735 A2 | 10/2001 |
| EP | 1 145 736 A2 | 10/2001 |
| GB | 1 161 579 | 8/1969 |
| WO | WO 92/20402 | 11/1992 |
| WO | WO 99/06108 | 2/1999 |
| WO | WO 99/34758 | 7/1999 |
| WO | WO 00/13743 | 3/2000 |
| WO | WO 00/40295 | 7/2000 |
| WO | WO 01/10369 | 2/2001 |
| WO | WO 01/28622 | 4/2001 |
| WO | WO 01/39830 | 6/2001 |
| WO | WO 01/60450 | 8/2001 |
| WO | WO 01/97906 | 12/2001 |
| WO | WO 02/05590 | 1/2002 |
| WO | WO 02/056637 | 7/2002 |
| WO | WO 02/083207 | 10/2002 |
| WO | WO 02/083208 | 10/2002 |
| WO | WO 02/083233 | 10/2002 |
| WO | WO 03/026739 | 4/2003 |
| WO | WO 03/076012 | 9/2003 |
| WO | WO 2004/043536 | 5/2004 |
| WO | WO 2004/052459 A1 | 6/2004 |

OTHER PUBLICATIONS

Written Opinion of the International Preliminary Examining Authority, International Application No, PCT/US2004/014804, filed May 12, 2004.

Notification of Transmittal of the International Preliminary Report on Patentability, International Application No. PCT/US2004/014804, filed May 12, 2004.

"Surgical Process," Animation Screenshots from http://www.cochlearamerica.com/800.asp, 7 pgs. (last printed Feb. 3, 2004).

"Candidates Brochure," http://www.cochlearameerica.com/pdfs/candidatebrochglobal.pdf, 14 pgs. (Aug. 19, 2002).

"Research and Development," http://www.cochlearamericas.com/384.asp, 1 pg. (last printed Feb. 3, 2004).

"The World Leader in cochlear implants—revolutionizing hearing for adults and infants," http://www.cochlear.com, 1 pg. (last printed Feb. 3, 2004).

"Cochlear: innovator of the Nucleus 3 cochlear implant system," http://www.cochlearamericas.com, 1 pg. (last printed Feb. 3, 2004).

"What is a Cochlear Implant," http://www.cochlearamericas.com/What/161.asp, 1 pg. (last printed Feb. 3, 2004).

"ESPrit 3G Speech Processor," http://www.cochlearamericas.com/591.asp, 2 pgs. (last printed Feb. 3, 2004).

"Nucleus 3 System," http://www.cochlearamericas.com/Products/465.asp, 1 pg. (last print Feb. 3, 2004).

"Internal Components: Nucleus 24 Cochlear Implants," http://www.cochlearamericas.com/374.asp, 1 pg. (last printed Feb. 3, 2004).

"Nucleus 24 Contour," http://www.cochlearamericas.com/568.asp, 2 pgs. (last printed Feb. 3, 2004).

"Nucleus 24 M," http://www.cochlearamericas.com/372.asp, 1 pg. (last printed Feb. 3, 2004).

"Nucleus 24 K," http://www.cochlearamericas.com/371.asp, 1 pg. (last printed Feb. 3, 2004).

"Nucleus 24 Double Array," http://www.cochlearamericas.com/370.asp, 1 pg. (last printed Feb. 3, 2004).

"Nucleus 24 ABI: Auditory Brainstem Implant," http://www.cochleararnericas.com/373.asp, 2 pgs. (last printed Feb. 3, 2004).

"Nucleus Speech Processors," http://www.cochlearamericas.com/629.asp, 1 pg. (last printed Feb. 3, 2004).

"Sprint: body worn speech processor," http://www.cochlearamericas.com/1010.asp, 1 pg. (last printed Feb. 3, 2004).

"Cochlear," http://www.cochlearamericas.com/Recipients/978.asp, 3 pgs. (last printed Feb. 3, 2004).

Communication from corresponding European Patent Application Serial No. 04751949.1-2310 dated Nov. 4, 2008 (4 pages).

* cited by examiner

IMPLANTABLE MEDICAL DEVICE WITH A NONHERMETIC BATTERY

This application is a divisional of U.S. patent application Ser. No. 10/835,233, filed Apr. 29, 2004, now U.S. Pat. No. 7,263,401 which claims the benefit of U.S. Provisional Application Ser. No. 60/471,262, filed on May 16, 2003. The entire content of each of these applications is incorporated herein by reference.

TECHNICAL FIELD

The invention relates to medical devices, and more particularly, to implantable medical devices.

BACKGROUND

Depending on the application for which they are implanted in a patient, implantable medical devices (IMDs) may include a variety of electrical and/or mechanical components. Typically, an IMD includes a rigid housing that houses all of its components, which are generally fragile, to protect the components from forces to which they would otherwise be exposed when implanted within the human body. In order to avoid potentially harmful interactions between the components and bodily fluids, e.g., corrosion, IMD housings are typically hermetically sealed. Many IMD housings are fabricated from titanium because of its desirable rigidity and biocompatibility.

The size and shape of an IMD housing is dependent on the sizes and shapes of the components of the IMD. Large components common to most IMDs include a battery and a circuit board that carries digital circuits, e.g., integrated circuit chips and/or a microprocessor, and analog circuit components. Attempts have been made to reduce the size of the IMD housing by reducing the size of these components, changing the shape of these components, and organizing these components within the IMD housing to avoid empty space within the housing.

However, the functional and safety requirements of IMDs have limited attempts to reduce the size and improve the shape of rigid IMD housings. For example, many types of batteries useful for powering an IMD can emit substances that would be harmful to the patient in which the IMD is implanted and to the other components of the IMD. Consequently, existing IMDs typically use hermetic batteries, e.g., batteries within a hermetically sealed housing or case, as a source of power. However, the need to make the housing or case of the battery hermetic limits the thinness and shapes that the battery may have, e.g., due to need for hermetic feedthroughs and the type of welding required for a hermetic housing or case. These limits to the size and shape that a hermetic battery may have in turn limit the ability of IMD designers to reduce the size and shape of IMD housings.

Consequently, the size, shape and rigidity of IMD housings still greatly limit the locations within the human body where an IMD can be practically implanted. Due to these limitations, an IMD is typically implanted within the abdomen, upper pectoral region, or subclavicular region of a patient. Leads or catheters must be used in order to deliver therapy or monitor a physiological parameter at a location of the body other than where the IMD is implanted. Implantation and positioning of leads and catheters can be difficult and time-consuming from the perspective of a surgeon, particularly where the IMD is located a significant distance from the treatment or monitoring site. Moreover, the increased surgical time, increased surgical trauma, and increased amount of implanted material associated with the use of leads and catheters can increase the risk to the patient of complications associated with the implantation of an IMD.

For example, IMDs that are used to treat or monitor the brain, e.g., to deliver deep brain stimulation (DBS) therapy, are implanted some distance away from the brain, e.g., within the subclavicular region of patients. The long leads that connect the implantable medical device to electrodes implanted within the brain require tunneling under the scalp and the skin of the neck, thereby requiring extensive surgery and a prolonged amount of time under general anesthesia during the implant procedure, as well as increased recovery time. In some cases, tunneling the leads under the scalp and skin of the neck requires an additional surgical procedure under general anesthesia. The lengthy tract along the leads is more susceptible to infection, and the leads can erode the overlying scalp, forcing removal so that the scalp can heal. Further, the long leads running under the scalp and through the neck are more susceptible to fracture due to torsional and other forces caused by normal head and neck movements.

SUMMARY

In general, the invention is directed to an implantable medical device (IMD) including a nonhermetic battery, i.e., a battery that is contained within a nonhermetic housing or other nonhermetic enclosure. The IMD includes components and a power source module that includes the nonhermetic battery. The nonhermetic battery delivers power to the components via an electrical conductor that extends from the nonhermetic battery to the components. In some embodiments the IMD may comprise a modular IMD. In those embodiments, the IMD includes a control module that includes the components within a control module housing and an interconnect member through which the electrical conductor extends to couple the control module and the power source module. In some cases, the components may comprise control electronics that control the functioning of the IMD.

Conventionally, nonhermetic batteries are not used in IMDs due to the potential hazard to the components within the IMD. The nonhermetic battery may leak substances that contain corrosive compounds, such as vaporized organic solvents, gasses produced during operation of the battery, and liquid electrolytes including salts. The substances may move from the nonhermetic battery to the components within the IMD where the corrosive compounds could cause damage. The damage would not only be harmful to the IMD, but could potentially be harmful to a patient in whom the IMD is implanted. For example, the substances from the nonhermetic battery that contain corrosive compounds may enter the patient's body. In addition, the damaged IMD may malfunction, e.g., and abruptly quit delivering therapy or deliver an inappropriate therapy to the patient.

An embodiment of the invention described herein includes a barrier within the IMD to substantially impede movement of substances from the nonhermetic battery to the components. The barrier may include, for example, a hermetic feedthrough through which the electrical conductor extends, a gel, a polymer, or a solid electrolyte within the nonhermetic battery, and a seal member. The barrier may also be a material that encapsulates the nonhermetic battery and a getter within a housing of the power source module. In general, a getter is a material which, when used in a closed container, absorbs or reacts with the substance in the container to neutralize the substance. A getter may be a getter for one substance and may not have any effect upon another substance.

In embodiments including the control module and the interconnect member, the barrier may include a material that fills at least a portion of a void defined by the interconnect member and a getter within the interconnect member or the control module housing. The length and/or the cross-sectional area of the interconnect member may also act as a barrier; in some embodiments the interconnect member is crimped to create a reduced-cross-sectional area region that serves to restrict the movement of substances. The IMD may include one of the barriers listed above or any combination of the barriers to impede the movement of substances from the nonhermetic battery.

In one embodiment, the invention is directed to an implantable medical device comprising components and a power source module. The power source module includes a nonhermetic battery. An electrical conductor delivers power from the nonhermetic battery to the components. A barrier that substantially impedes movement of substances from the nonhermetic battery to the components is located between the components and the nonhermetic battery.

In another embodiment, the invention is directed to an implantable medical device comprising components and a power source module. The power source module includes a power source module housing and a nonhermetic battery within the power source module housing. An electrical conductor delivers power from the nonhermetic battery to the components. A material that substantially impedes movement of substances from the nonhermetic battery to the components is included within the power source module housing.

In another embodiment, the invention is directed to an implantable medical device comprising components and a power source module. The power source module includes a nonhermetic battery. An electrical conductor delivers power from the nonhermetic battery to the components. A means for substantially impeding movement of substances from the nonhermetic battery to the components is included in the implantable medical device.

In another embodiment, the invention is directed to an implantable medical device comprising a control module and a power source module. The control module includes a control module housing and components within the control module housing. The power source module includes a power source module housing and a nonhermetic battery within the power source module housing. An interconnect member couples the control module and the power source module. An electrical conductor extends through the interconnect member from the nonhermetic battery to the components to deliver power from the nonhermetic battery to the components.

In a further embodiment, the invention is directed to a method of manufacturing an implantable medical device. The method comprises forming a control module including components and forming a control module housing to house the components. The method further comprises forming a power source module including a nonhermetic battery and forming a power source module housing to house the nonhermetic battery. The method also comprises forming an interconnect member to couple the control module and the power source module. The interconnect member includes an electrical conductor that extends through the interconnect member to deliver power from the nonhermetic battery to the components.

The invention may be capable of providing one or more advantages. For example, a barrier that substantially impedes movement of substances from the nonhermetic battery to the components allows the nonhermetic battery to be used safely within the IMD. One or more barriers block, absorb, and/or dissipate the corrosive compounds included in the substances, thereby preventing damage to the components and harm to the patient in which the IMD is implanted.

The nonhermetic battery within the IMD may provide a number of advantages relative to a hermetic battery. For example, the nonhermetic battery may permit significant reductions in the thickness of the power source module housing and the overall profile of the IMD as well as a reduction in the overall size of the IMD. The reduced size and profile thickness allows the IMD to be more cosmetically appealing, comfortable, and clinically acceptable when implanted within a patient. In particular, the IMD may create a much smaller and less noticeable protrusion when implanted in the patient, and may reduce the likelihood of skin erosion above the implanted IMD. In addition, the nonhermetic battery may have increased longevity and energy density per cubic centimeter when compared to hermetic batteries.

The thin nonhermetic battery may also increase packaging efficiency. A much larger choice of materials are available for the nonhermetic battery than for a hermetic battery. A wider variety of battery form factors are also possible, including the potential to use a foil-pack flexible battery. The reduced packaging and variety of material choices associated with the nonhermetic battery significantly reduces the cost of manufacturing the IMD, potentially by as much as ten times relative to some existing IMDs.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
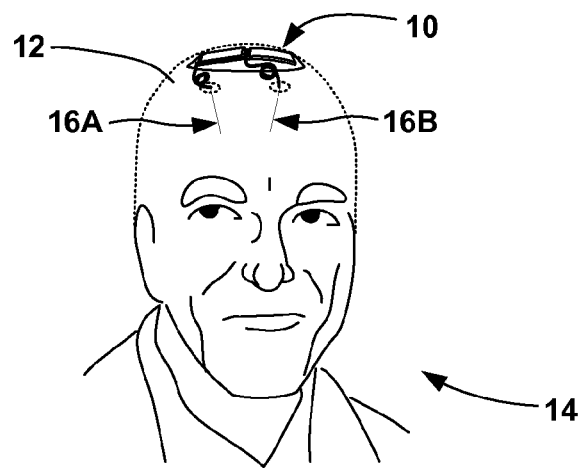
FIG. 1 is a conceptual diagram illustrating an example implantable medical device (IMD) implanted on a cranium of a patient.

FIG. 1 is a conceptual diagram illustrating an example implantable medical device (IMD) 10 that includes a power source module and a nonhermetic battery housed within a power source module housing. The nonhermetic battery may reduce a thickness and overall size of the power source module housing and thereby reduce a profile of IMD 10. The reduced profile allows IMD 10 to be more cosmetically appealing, comfortable, and clinically acceptable when implanted, for example, on the cranium 12 of a patient 14. Other embodiments of IMD 10 permit the device to be implanted at many other locations within the body of patient 14 that do not present an adequate profile for conventional implantable medical devices.

The nonhermetic battery may provide advantages beyond the reduced profile of IMD 10. For example, compared to a hermetic battery, the nonhermetic battery expands the material and form factor choices available for the power source module housing. Increased packaging efficiency and the ability to select less expensive materials allows the nonhermetic battery to significantly reduce the cost of manufacturing IMD 10. In addition, the nonhermetic battery increases longevity and energy density per cubic centimeter.

In general, a nonhermetic battery is built to perform substantially similar to a hermetic battery. For example, a nonhermetic battery may initially perform just as well in a helium leak test as a hermetic battery. However, unlike hermetic batteries which have enclosures that include welded, glassed, or braised seals, nonhermetic batteries typically have enclosures that include crimped seals. Over time, the crimped seals have a tendency to break down and leak substances, such as vaporized organic solvents, gasses produced during operation of the battery, and liquid electrolytes including salts.

The substances that may leak from the nonhermetic battery may contain corrosive compounds harmful to IMD 10 and patient 14. IMD 10 includes a barrier to substantially impede the movement of substances from the nonhermetic battery to components in IMD 10. The barrier ensures that the substances from the nonhermetic battery will not harm patient 14 in which IMD 10 is implanted and will not damage the components. In some embodiments, the components comprise control electronics that control the functioning of the IMD. Several embodiments of the barrier will be described in greater detail below.

The nonhermetic battery can be applied within an IMD of any structure. For purposes of illustration, however, the invention will be described herein as a modular IMD housed in a member that at least partially encapsulates one or more housings of the modules and, and generally serves to provide a smooth interface between the modules and the body tissue. As will be described in greater detail below, IMD 10 comprises a plurality of separately housed and flexibly interconnected modules. By distributing components of IMD 10 among modules rather than including them within a single, rigid housing, the IMD may be shaped and configured for implantation at locations within patient 14 for which implantation of conventional IMDs is deemed undesirable or inapplicable. Further, the flexibility of the interconnection between modules of IMD 10 may allow multiples degrees of freedom of movement between the modules, which in turn may allow the implantable medical device to conform to such areas, and in particular embodiments, to conform to surfaces within patient 14 such as the surface of cranium 12.

In the illustrated example, modular IMD 10 is coupled to two leads 16A and 16B (collectively "leads 16") that extend through holes within cranium 12, and into the brain of patient 14. In exemplary embodiments, each of leads 16 carries a plurality of electrodes, and IMD 10 delivers stimulation to the brain of patient 14 via the electrodes. Modular IMD 10 may be coupled to any number of leads 16, and in some embodiments is not coupled to any leads 16. In some embodiments, for example, IMD 10 may carry integrated electrodes.

Because modular IMD 10 can be implanted on cranium 12 of patient 14 rather then more remotely from the brain of patient 14, such as within a subclavicular region of patient 14, the problems associated with the use of long leads needed to allow a remotely implanted IMD to access the brain may be diminished or avoided. These problems include the requirement of tunneling under the scalp and the skin of the neck, increased surgery and recovery time, an additional procedure under general anesthesia, risk of infection or skin erosion along the track through which the leads are tunneled, and risk of lead fracture due to torsional and other forces caused by normal head and neck movements.

Figure 2:
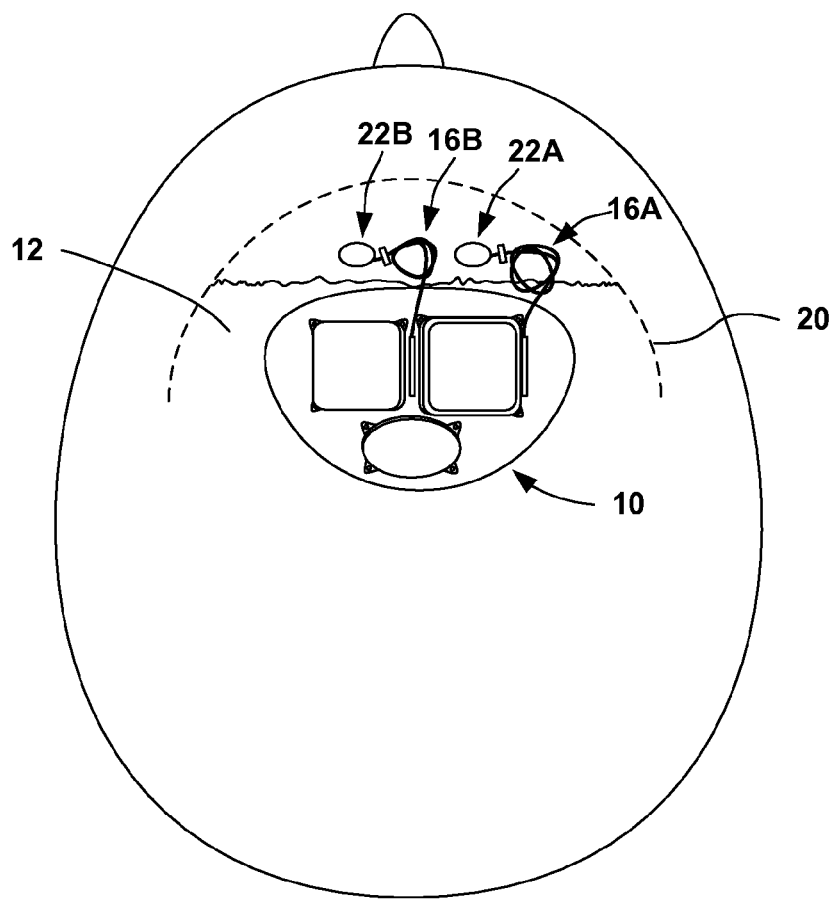
FIG. 2 is a top-view diagram further illustrating the IMD from FIG. 1 implanted on the cranium of the patient.

FIG. 2 is a top-view diagram further illustrating IMD 10 implanted on cranium 12 of the patient 14. In order to implant modular IMD 10 on cranium 12, an incision 20 is made through the scalp of patient 14, and a resulting flap of skin is pulled back to expose the desired area of cranium 12. The incision may, as shown in FIG. 2, be generally shaped like a "C." Such an incision is commonly referred to as a "C-flap" incision.

Holes 22A and 22B (collectively "holes 22") are drilled through cranium 12, and leads 16 are inserted through holes 22 and into the brain of patient 14. Caps such as burr hole caps may be placed over holes 22 as is known in the art. Leads 16 are connected to modular IMD 10, either directly or via a lead extension, and modular IMD 10 is placed at least partially within a pocket formed using a hand or a tool beneath the scalp behind holes 22.

Once positioned as desired on cranium 12 within the pocket, modular IMD 10 may then be fixed to cranium 12 using an attachment mechanism such as bone screws. The skin flap may be closed over modular IMD 10, and the incision may be stapled or sutured. The location on cranium 12 at which IMD 10 is illustrated as implanted in FIG. 2 is merely exemplary, and IMD 10 can be implanted anywhere on the surface of cranium 12.

Because of the flexibility that may be provided by interconnect members of IMD 10 and/or a member of IMD 10 that at least partially encapsulates the modules of IMD 10 and provides a smooth interface between the modules and body tissue, the IMD may be manipulated during implantation such that it conforms to cranium 12. For example, in some embodiments a surgeon can manipulate modular IMD 10 into conformance with cranium 12 while IMD 10 is on cranium 12 and fix modular IMD 10 into place using bone screws or the like. In other embodiments, the clinician may manipulate modular IMD 10 into conformance with cranium 12 with IMD 10 on and/or off of cranium 12, and IMD 10 may substantially retain the form into which it is manipulated.

As mentioned above, modular IMD 10 may deliver stimulation to the brain of patient 14 to, for example, provide deep brain stimulation (DBS) therapy, or to stimulate the cortex of the brain. Cortical stimulation may involve stimulation of the motor cortex. Modular IMD 10 may be used to treat any nervous system disorder including, but not limited to, epilepsy, pain, psychological disorders including mood and anxiety disorders, movement disorders (MVD), such as, but not limited to, essential tremor, Parkinson's disease, and neurodegenerative disorders.

However, modular IMD 10 is not limited to delivery of stimulation to the brain of patient, and may be employed with leads 16 deployed anywhere in the head or neck including, for example, leads deployed on or near the surface of the skull, leads deployed beneath the skull such as near or on the dura mater, leads placed adjacent cranial or other nerves in the neck or head, or leads placed directly on the surface of the brain. Moreover, modular IMD 10 is not limited to implantation on cranium 12. Indeed, modular IMD 10 may be implanted anywhere within patient 14. For example, modular IMD 10 can be implanted within the neck of patient 14, and deliver stimulation to the vagus nerve or the cervical region of the spinal cord.

Modular IMD 10 may alternatively be implanted within a pectoral region or the abdomen of patient 14 to act as a diaphragmatic pacer, or to provide any of the monitoring and therapy delivery functions known in the art to be associated with cardiac pacemakers. Further, modular IMD 10 may be implanted in the upper buttock region and deliver spinal cord, urological or gastrological stimulation therapy, or may be configured to be implanted within the periphery, e.g., limbs, of patient 14 for delivery of stimulation to the muscles and/or peripheral nervous system of patient 14. Additional implant locations may include the abdomen, e.g., for gastric stimulation. As is the case with cranium 12, the modularity of IMD 10 may enable implantation at some of these example locations for which implantation of conventional IMDs is generally deemed undesirable.

Modular IMD 10 is not limited to embodiments that deliver stimulation. For example, in some embodiments modular IMD 10 may additionally or alternatively monitor one or more physiological parameters and/or the activity of patient 14, and may include sensors for these purposes. Where a therapy is delivered, modular IMD 10 may operate in an open loop mode (also referred to as non-responsive operation), or in a closed loop mode (also referred to as responsive). Modular IMD 10 may also provide warnings based on the monitoring.

As discussed above, the ability of a modular IMD 10 according to the invention to be implanted close to a region within patient 14 to be monitored enables the use of shorter leads 16. Shorter leads 16 may advantageously improve the accuracy of such sensors by reducing noise attributable to leads 16. Shorter leads 16 may also advantageously reduce the negative affects of imaging techniques such as magnetic resonance imaging "MRI" on a person implanted with IMD 10. Within an MRI machine, leads act as antennas positioned very close to an antenna tower, therefore using shorter leads 16 reduces an amount of energy induced onto IMD 10 from the MRI machine.

Further, in some embodiments modular IMD 10 can additionally or alternatively deliver a therapeutic agent to patient 14, such as a pharmaceutical, biological, or genetic agent. Modular IMD 10 may be coupled to a catheter, and may include a pump to deliver the therapeutic agent via the catheter.

Figure 3:
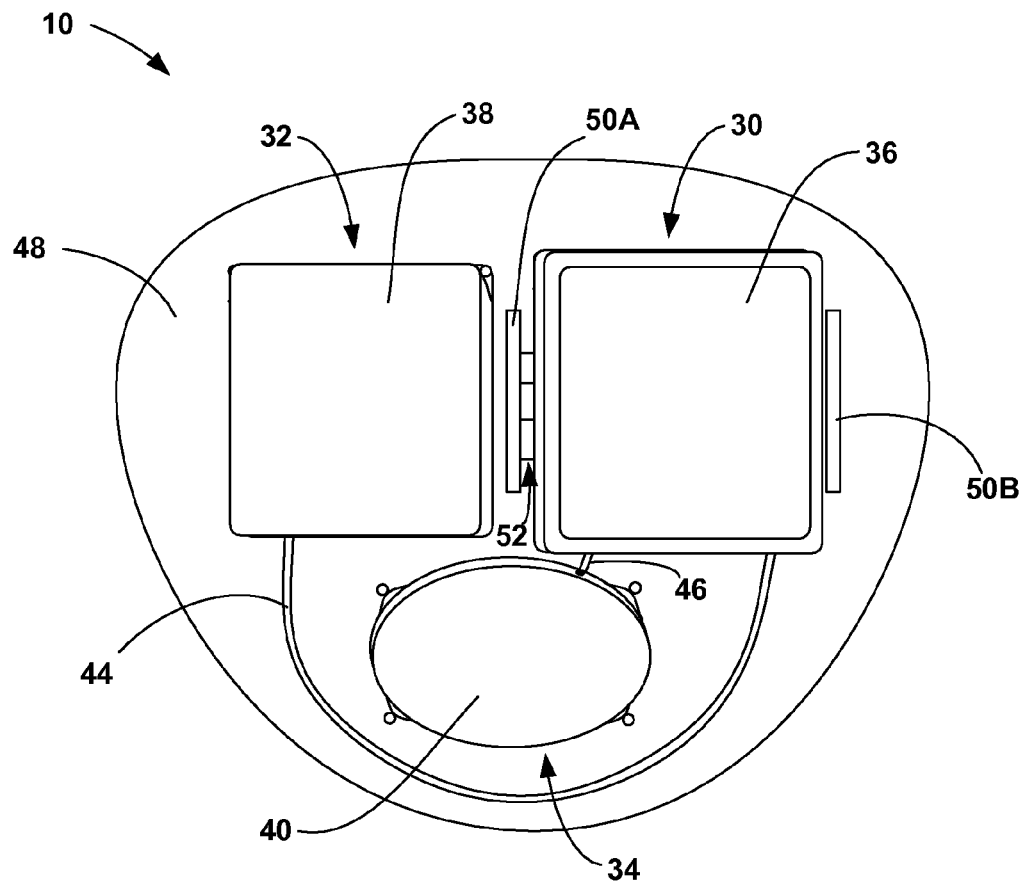
FIG. 3 is a top-view diagram further illustrating a modular IMD.

FIG. 3 is a top-view diagram further illustrating modular IMD 10. In the illustrated embodiment, modular IMD 10 includes three modules: a control module 30, a power source module 32, and a recharge module 34. As shown in FIG. 3, modules 30, 32 and 34 include separate housings 36, 38 and 40, respectively.

Control module 30 includes components within the housing. In some embodiments, the components comprise control electronics, e.g., electronics that control the monitoring and/or therapy delivery functions of modular IMD 10, such as a microprocessor. Control module 30 may also include circuits for telemetry communication with external programmers or other devices within the housing. Housing 36 of control module 30 may be hermetic in order to protect the components therein, and in exemplary embodiments is formed of a rigid material, such as titanium, stainless steel, or a ceramic. In exemplary embodiments, housing 36 is a low-profile, concave housing to substantially conform to a patient's cranium.

Power source module 32 includes a nonhermetic battery. A nonhermetic battery is a battery contained within a nonhermetic housing or other nonhermetic enclosure, e.g., a housing or enclosure, as described above. The nonhermetic battery is then further housed within housing 38. The nonhermetic battery provides power for components of other modules, such as the components within control module 30. The nonhermetic battery may be any nonhermetic battery suitable for use within an IMD. In an exemplary embodiment, the nonhermetic battery comprises a rechargeable Lithium Ion battery with a flexible foil pack construction to more easily fit within housing 38, which may be less than approximately 5 millimeters thick in a direction normal to a major plane of the housing. The major plane of housing 38 may include an approximately one square inch (6.5 square centimeters) surface area. Housing 38 may be hermetic, and may be formed of titanium, stainless steel, or a ceramic. Power source module 32 may include an insulator within housing 38 to electrically isolate housing 38 from the nonhermetic battery.

Including the nonhermetic battery in power source module 32 reduces a thickness and overall size of housing 38, which may then reduce a profile of IMD 10. The low profile of IMD 10 permits IMD 10 to be deployed effectively, comfortably and cosmetically within patient 14. In one embodiment of the invention, IMD 10 including the nonhermetic battery has a maximum thickness of between approximately 1 millimeter and approximately 5 millimeters. The use of a reduced profile may reduce the risk of infection, skin erosion and cosmetic issues related to the implantation of IMD 10.

Where the nonhermetic battery comprises a rechargeable nonhermetic battery, modular IMD 10 may include recharge module 34. Recharge module 34 includes a recharge coil (not shown) within housing 40. The recharge coil inductively receives energy from an external recharging unit (not illustrated) through the skin of patient 14 to recharge the nonhermetic battery. The recharge coil may be formed of windings of copper or another highly conductive material. Housing 40 need not be hermetic, and may be formed of materials such as silicone, polymers and ceramics.

Housings 36, 38 and 40 may have any shape, including the round, coin shape and rectangular shapes with rounded edges illustrated in FIG. 3. Further, one or more surfaces of one or more of housings 36, 38 and 40 may be concave along at least one axis, and preferably two axes.

Modules 30, 32 and 34 can be configured in a variety of ways, and the configuration illustrated in FIG. 3 is merely exemplary. Further, modular IMD 10 can include any number of modules, and may include other types of modules instead of or in addition to a control module 30 and a recharge module 34. For example, modular IMD 10 can include a module within another module, such as power source module 32 within control module 30. In addition, modular IMD 10 can include additional power source modules, modules that include additional memory that is accessible by the components, modules that include reservoirs for storing therapeutic agents and pumps for delivering therapeutic agents to patient 14, and modules that include sensors sensing physiological parameters, such as pressures or blood flows, or the activity level of patient 14.

Power source module 32 is coupled to control module 30 by a flexible interconnect member 44, which encloses an electrical conductor that allows transmission of energy from the nonhermetic battery of power source module 32 to components such as the components within control module 30. In embodiments where energy is transferred via a DC voltage on the electrical conductor, it may be necessary to make flexible interconnect member 44 hermetic. In embodiments in which flexible interconnect member 44 is hermetic, flexible interconnect member 44 may be made of titanium, stainless steel, or nitinol. In embodiments where energy is transferred via a charge-balance voltage on the electrical conductor, such as an AC voltage, flexible interconnect member 44 need not be hermetic, and may be made of any material including silicone or various polymers.

In the illustrated embodiment, the components of control module 30 regulate the recharging and discharging of the nonhermetic battery within power source module 32. Consequently, as shown in FIG. 3, recharge module 34 is coupled to control module 30 by a flexible interconnect member 46 that encloses an electrical conductor that allows transmission of energy inductively received by the recharge coil within recharge module 34 to control module 30. Because the energy is transferred on the electrical conductor via a charge-balanced voltage, flexible interconnect member 46 need not be hermetic, and may be made of any material including titanium, stainless steel, nitinol, ceramics, silicone or various polymers.

Interconnect members 44 and 46 are flexible. In some embodiments, as indicated above, interconnect members 44 and 46 are made of a flexible material such as silicone, a flexible polymer, or nitinol. In embodiments where flexible member 44 is hermetic and made of a substantially less flexible material, such as titanium or stainless steel, the flexibility of interconnect member 44 is provided by the configuration and/or construction of flexible interconnect member 44.

Interconnect member 44 is flexible in a plurality of directions to provide modules 30 and 32 with multiple degrees of freedom of motion with respect to each other. In exemplary embodiments, interconnect member 44 provides at least three degrees of motion, and the degrees of motion provided include rotational motion.

As shown in FIG. 3, modular IMD 10 includes a member 48, which may be flexible and made of a soft biocompatible material. Member 48 at least partially encapsulates one or more of housings 36, 38 and 40, and generally serves to provide a smooth interface between the modules and the body tissue. Member 48 may integrate modules 30, 32 and 34 into a desired form factor, but, where flexible, allow relative intermodule motion. In some embodiments, member 48 incorporates mechanical features to restrict intermodule motion to certain directions or within certain ranges. Member 48 may be made from silicone, and in some embodiments may be made from two or more materials of differing flexibility, such as silicone and a polyurethane. An exemplary polyurethane for this purpose is Tecothane®, which is commercially available from Hermedics Polymer Products, Wilmington, Mass. Member 36 may also be referred to as an "overmold," but use of the term "overmold" herein is not intended to limit the invention to embodiments in which member 36 is a molded structure. Member 36 may be a molded structure, or may be a structure formed by any process.

Member 48 can be shaped to contour to cranium 12, e.g., may be concave along at least one axis, and may be contoured at its edges to prevent skin erosion on the scalp of patient 14. The flexibility and shape of member 48 may, in some embodiments, improve the comfort and cosmetic appearance of modular IMD 10 under the scalp, and may make IMD 10 more clinically acceptable by, for example, reducing the likelihood of skin erosion.

In the illustrated embodiment, modular IMD 10 also includes lead connector modules 50A and 50B (collectively "lead connector modules 50") formed within member 48 to receive leads 16 or lead extensions coupled to leads 16. Conductors 52 extend from lead connector modules 50 to hermetic feedthroughs (not illustrated) within housing 36 of control module 30. Lead connector modules 50 may be formed anywhere within member 48. In embodiments where member 48 includes a rigid material in addition to a flexible material, the rigid material may form at least part of lead connector modules 50 to secure leads 16 or lead extensions, and to protect conductors 52 from damage that may result from flexing within member 48.

Figure 4:
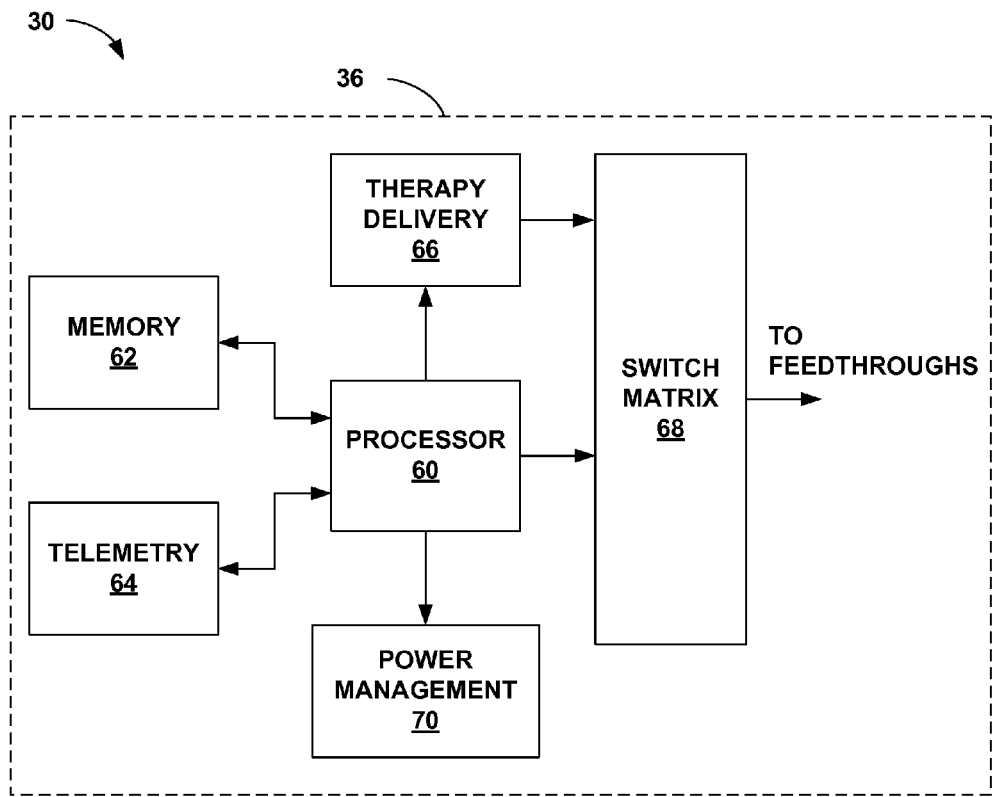
FIG. 4 is a block diagram illustrating a control module of the modular IMD from FIG. 3.

FIG. 4 is a block diagram illustrating control module 30 of modular IMD 10. As described above, control module 30 includes components, such as control electronics that control the functioning of modular IMD 10 within housing 36. The components include a processor 60, which may take the form of a microprocessor, digital signal processor (DSP), application specific integrated circuit (ASIC), field-programmable gate array (FPGA), or other logic circuitry.

Control module 30 also includes a memory 62, such as a read-only memory (ROM), random access memory (RAM), electronically-erasable programmable ROM (EEPROM), flash memory, or the like. Memory 62 may store program instructions that may be executed by processor 60 and thereby control the functioning of modular IMD 10. Processor 60 may also store data colleted during treatment and/or monitoring of patient 14 within memory 62.

In some embodiments, control module 30 includes telemetry circuitry 64, which enables processor 60 to communicate with other devices such as an external programming device via radio-frequency communication. Telemetry circuitry 64 may include a telemetry coil (not illustrated), which may be fabricated of windings of copper or another highly conductive material. The configuration and location of the telemetry coil within housing 36 may be dictated by the available space within housing 36 and the communication requirements of telemetry circuitry 64.

In some embodiments, modular IMD 10 delivers electrical stimulation, and more particularly, control module 30 includes therapy delivery circuitry 66 within housing 36 that generates electrical stimulation. In exemplary embodiments, therapy delivery circuitry 66 comprises circuits for the generation of electrical stimulation in the form of pulses, such as capacitors and switches. In embodiments in which modular IMD 10 is a neurostimulator coupled to leads 16 that include a plurality of electrodes, therapy delivery circuitry 66 may deliver the pulses to a switch matrix 68, which comprises an array of switches. In such embodiments, processor 60 interacts with switch matrix 68 to select electrodes for delivery of generated stimulation pulses. Based on the selections made by processor 60, switch matrix 68 delivers the pulses to conductors that pass through feedthroughs in housing 36 and to electrical contacts on leads 16 that are electrically coupled to the desired electrodes carried by leads 16.

The illustrated components of control module 30 receive energy from the nonhermetic battery within power source module 32 via interconnect member 44 (FIG. 3). In some embodiments in which the nonhermetic battery is rechargeable, control module 30 receives energy inductively captured by recharge module 34 via interconnect member 46, and includes power management circuitry 70 that controls the recharging and discharging of the nonhermetic battery. Power management circuitry 70 may ensure that the nonhermetic battery is not overcharged, over-discharged, or harmed. In some embodiments, power management circuitry 70 includes circuits to measure voltages, currents or temperatures associated with the nonhermetic battery, or rates of change of these parameters, and controls recharging and discharging according to the measured values. Power management circuitry 70 may also include circuits, such as rectifier circuits, for converting charge-balanced voltages, e.g., AC voltages, provided by a recharge coil (not shown) into net DC voltages for recharging the nonhermetic battery.

Figure 5:
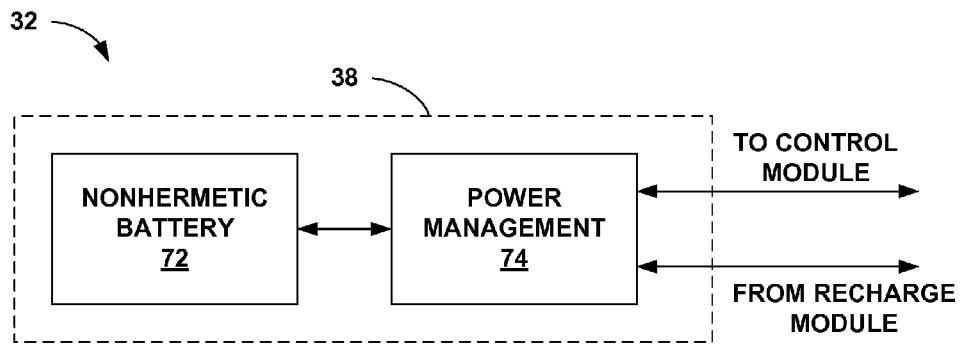
FIG. 5 is a block diagram illustrating a power source module of the modular IMD from FIG. 3.

FIG. 5 is a block diagram illustrating power source module 32 of modular IMD 10. Power source module 32 includes a rechargeable nonhermetic battery 72 within housing 38. In the illustrated embodiment in which power source module 32 directly receives energy inductively captured by recharge module 34 via flexible interconnect member 44, power source module 32 also includes power management circuit 74 that controls the recharging and discharging of nonhermetic battery 72. As described above with reference to power management circuitry 70 of control module 30 illustrated in FIG. 4, power management circuitry 74 may ensure that nonhermetic battery 72 is not overcharged, over-discharged, or harmed. In some embodiments, power management circuitry 74 includes circuits to measure voltages, currents or temperatures associated with nonhermetic battery 72, or rates of change of these parameters, and controls recharging and discharging of nonhermetic battery 72 according to the measured values.

Power management circuitry 74 may also include circuits, such as rectifier circuits, for converting charge-balanced voltages, e.g., AC voltages, provided by a recharge coil (not shown) into DC voltages for recharging nonhermetic battery 72. In some embodiments in which interconnect member 44 is nonhermetic, power management circuitry 74 includes modulating circuits, i.e., circuits that enable power management circuit 74 to deliver energy to control module 30 in the form of charge-balanced voltages on an electrical conductor. In such embodiments, control module 30 includes circuits, such as rectifier circuits, to convert the charge-balanced voltages to DC voltages for use by components of control module 30.

FIGS. 6-11 are block diagrams illustrating example IMDs including barriers, in accordance with embodiments of the invention, that substantially impede movement of substances from a nonhermetic battery to components within the example IMDs. In some embodiments, the components comprise control electronics. The substances from the nonhermetic battery may contain corrosive compounds, such as vaporized organic solvents, gasses produced during operation of the battery, and liquid electrolytes including salts. The barriers impede the movement of substances from the nonhermetic battery to the components so that the corrosive compounds cannot cause damage. The damage would not only be harmful to the IMD, but could potentially be harmful to a patient in whom the IMD is implanted. For example, the substances from the nonhermetic battery that contain corrosive compounds may enter the patient's body. In addition, the damaged IMD may malfunction, e.g., abruptly quit delivering therapy or deliver inappropriate therapy to the patient.

The example IMDs may operate substantially similar to IMD 10 described above. Each of the barriers may be used individually or in combination with one another. For purposes of illustration, each of the IMDs illustrated in FIGS. 6-11 comprises one electrical conductor between the nonhermetic battery and the components. Typically, at least two electrical conductors are included to allow electrical isolation between a housing of the nonhermetic battery and a case of the IMD. In that way, the case of the IMD may be used as an electrical element for interaction with an electrode, for example. Again, the invention may be included in an IMD of any structure, but will be described herein as embodied within a modular IMD.

Figure 6A:
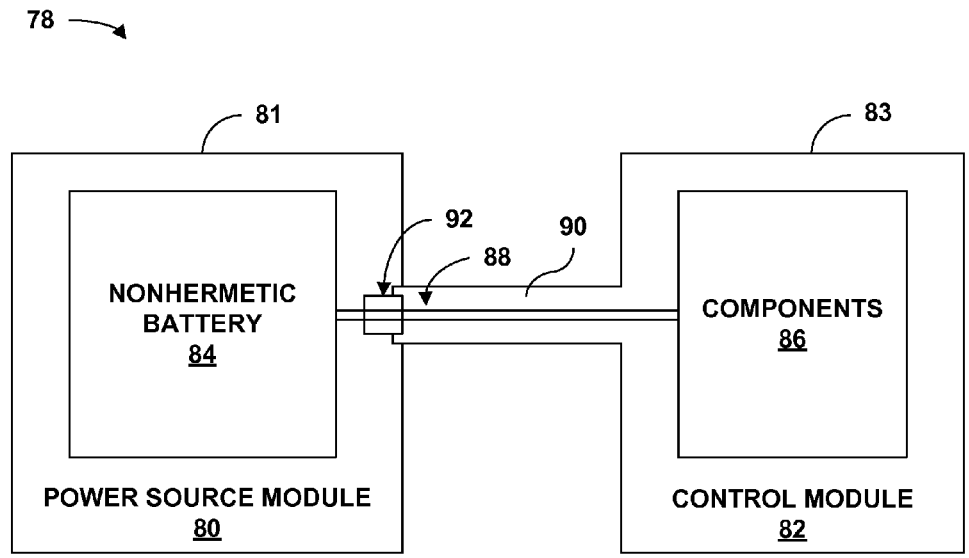
FIGS. 6-11 are block diagrams illustrating example IMDs including barriers to substantially impede movement of substances from a nonhermetic battery in accordance with various embodiments of the invention.
Figure 6B:
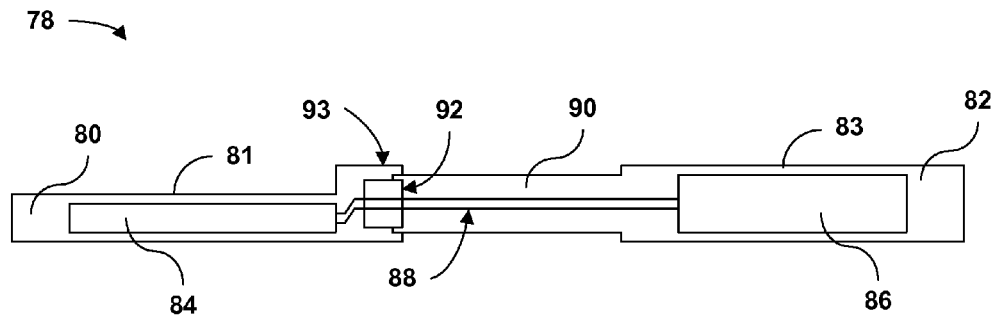

FIGS. 6A and 6B are block diagrams illustrating a top view and a side view, respectively, of an example IMD 78. IMD 78 includes a power source module 80 that includes a power source module housing 81 and a nonhermetic battery 84 within power source module housing 81. Additionally, IMD 78 further includes a control module 82 that includes a control module housing 83 and components 86 within control module housing 83. An electrical conductor 88 extends from nonhermetic battery 84 to components 86 and delivers power from nonhermetic battery 84 to components 86. Power source module 80 and control module 82 are coupled via an interconnect member 90, through which conductor 88 extends.

IMD 78 comprises a hermetic feedthrough 92 that acts as a barrier to substantially impede movement of substances, such as vaporized organic solvents, gasses produced during operation of the battery, and liquid electrolytes including salts, from nonhermetic battery 84 to components 86. Electrical conductor 88 extends through hermetic feedthrough 92 between nonhermetic battery 84 and components 86. As shown in FIGS. 6A and 6B, hermetic feedthrough 92 is positioned at an interface area 93 where power source module 80 and interconnect member 90 couple to each other. In that way, hermetic feedthrough 92 may ensure that no corrosive compounds included in the substances from nonhermetic battery 84 can leave power source module housing 81. As opposed to a nonhermetic feedthrough comprising a rivet that, over time, may allow the substances to leak, a hermetic feedthrough comprises a weld or a braise that maintains a substantially permanent air-tight seal.

As hermetic feedthrough 92 blocks the movement of substances from reaching components 86, at least a portion of hermetic feedthrough 92 is exposed to the corrosive compounds within the substances. The exposed portion of hermetic feedthrough 92 may be subject to corrosive effects, especially at contact points with power source module housing 81 and nonhermetic battery 84. Therefore, in order to connect hermetic feedthrough 92 to the positive pole of nonhermetic battery 84, a selected pin material must be able to avoid corrosion. For example, a Niobium pin may be prone to corrosion, but suitable corrosion-resistant pin materials may include Ti-6V-4Al, aluminum, or molybdenum. In addition, hermetic feedthrough 92 may comprise a suitable corrosion-resistant feedthrough glass material, such as Cabal-12.

In the illustrated embodiment, only one hermetic feedthrough 92 is used. Therefore, interconnect module 90 is a conductor in electrical contact with one of the poles of nonhermetic battery 84. In other embodiments, additional hermetic feedthroughs may be included in IMD 78. For example, if two hermetic feedthroughs are used, interconnect member 90 can be electrically insulated from nonhermetic battery 84. Additional feedthroughs may also be used to connect control module 82 to sensors in power source module 80. The sensors may detect temperature or, in the case of a voltage reference electrode, battery status.

Hermetic feedthrough 92 forms a part of power source module housing 81. However, hermetic feedthrough 92 in power source module housing 81 causes interface area 93 and interconnect member 90 to comprise thicknesses at least as thick as an outside cross-sectional area of hermetic feedthrough 92. As shown in FIG. 6B, power source module housing 81 remains thin until interface area 93. The illustrated embodiment allows IMD 78 to have a maximum thickness of between approximately 3 millimeters and approximately 8 millimeters.

Figure 7A:
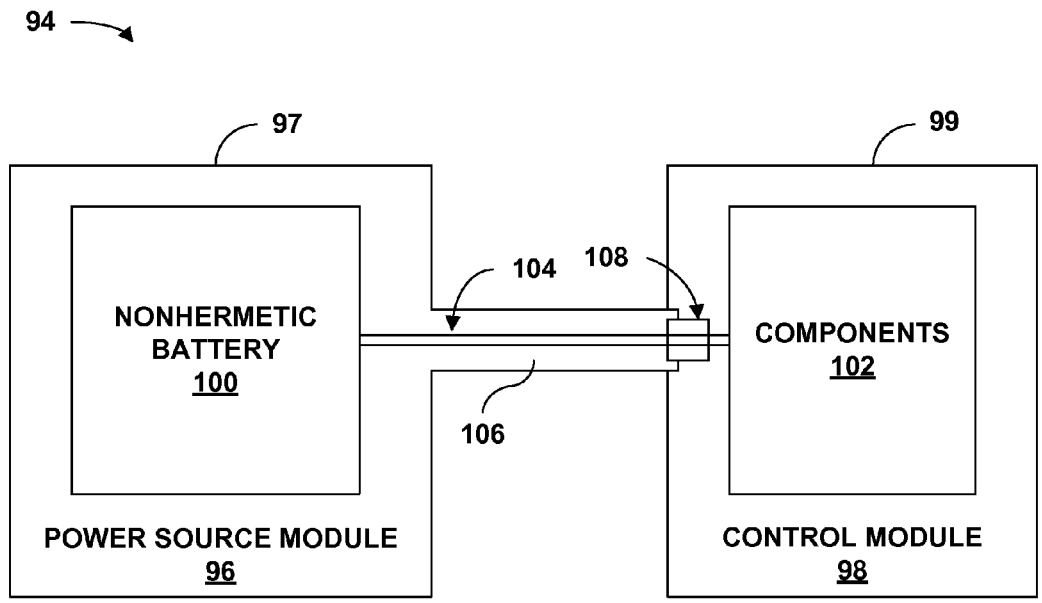
Figure 7B:
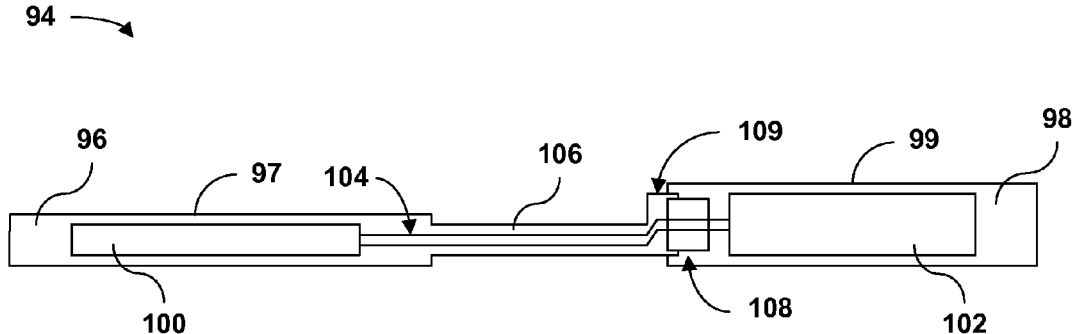

FIGS. 7A and 7B are block diagrams illustrating a top view and a side view, respectively, of another example IMD 94. IMD 94 includes a power source module 96 that includes a power source module housing 97 and a nonhermetic battery 100 within power source module housing 97. Additionally, IMD 94 further includes a control module 98 that includes a control module housing 99 and components 102 within control module housing 99. An electrical conductor 104 extends from nonhermetic battery 100 to components 102 and delivers power from nonhermetic battery 100 to components 102. Power source module 96 and control module 98 are coupled via an interconnect member 106, through which conductor 104 extends.

IMD 94 comprises a hermetic feedthrough 108 that acts as a barrier to substantially impede movement of substances from nonhermetic battery 100 to components 102. Electrical conductor 104 extends through hermetic feedthrough 108 between nonhermetic battery 100 and components 102. As shown in FIGS. 7A and 7B, hermetic feedthrough 108 is positioned at an interface area 109 where interconnect member 106 and control module 98 couple to each other. In that way, hermetic feedthrough 108 may ensure that no corrosive compounds included in the substances from nonhermetic battery 100 can enter control module housing 99. Hermetic feedthrough 108 may be substantially similar to hermetic feedthrough 92 described in reference to FIGS. 6A and 6B.

Hermetic feedthrough 108 forms a part of control module housing 99. However, hermetic feedthrough 108 in control module housing 99 causes interface area 109 of interconnect member 106 to comprise a thickness at least as thick as an outside cross-sectional area of hermetic feedthrough 108. As shown in FIG. 7B, power source module housing 97 and interconnect member 106, until interface area 109, comprise thicknesses less than an outside area of hermetic feedthrough 108. The illustrated embodiment allows IMD 94 to have a maximum thickness of between approximately 3 millimeters and approximately 8 millimeters In addition to the positions of hermetic feedthroughs 92 and 108 described above, a hermetic feedthrough may be located at any position along an interconnect member, such as interconnect member 106. The interconnect member may be constructed in two sections joined together by, for example, welding. Movement of substances from a nonhermetic battery may subject the welded areas of the interconnect member to corrosive effects. The hermetic feedthrough may be positioned between the two sections to block the movement of substances from damaging the welded areas of the interconnect member and components within the IMD.

Figure 8:
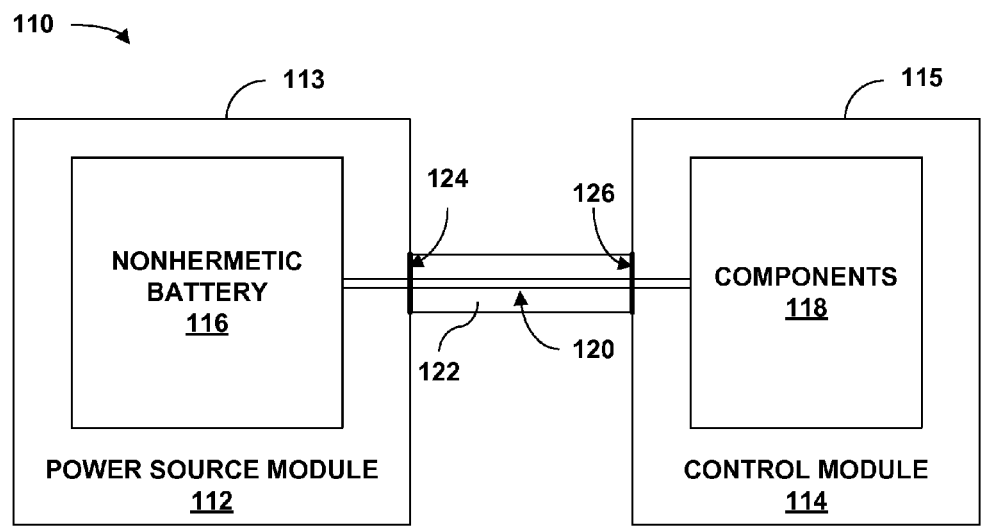

FIG. 8 is a block diagram illustrating a top view of an example IMD 110. IMD 110 includes a power source module 112 that includes a power source module housing 113 and a nonhermetic battery 116 within power source module housing 113. Additionally, IMD 110 further includes a control module 114 that includes a control module housing 115 and components 118 within control module housing 115. An electrical conductor 120 extends from nonhermetic battery 116 to components 118 and delivers power from nonhermetic battery 116 to components 118. Power source module 112 and control module 114 are coupled via an interconnect member 122, through which conductor 120 extends.

IMD 110 comprises a first seal member 124 and a second seal member 126 that act as barriers to substantially impede movement of substances from nonhermetic battery 116 to components 118. First seal member 124 is positioned within interconnect member 122 where interconnect member 122 couples to power source module 112. First seal member 124 blocks the movement of substances from leaving the power source module housing 113. Second seal member 126 is positioned within interconnect member 122 where interconnect member 122 couples to control module 114. Second seal member 126 blocks the movement of substances from entering the control module housing 115. In embodiments where interconnect member 122 comprises a cylindrical shape, first and second seals 124, 126 may comprise o-ring, gasket, or grommet seals. In some embodiments, only one of the first and second seal members is included within IMD 110. In other embodiments, a plurality of seal members may be positioned at a plurality of locations within IMD 110.

First and second seals 124, 126 may comprise materials with low permeability and high creep resistance. For example, these materials may be cross-linked crystalline materials that are either rigid or elastomeric. A partial list of rigid materials includes polypropylene, high density polyethylene, polyester, and engineering plastics such as polymers containing ether ketones (PEK, PEEK), polyether imide (PEI), polyamide imide (PAI), polyphenylene oxide (PPO), polyether sulfone (PES), and polyphenylene sulfide (PPS). A partial list of elastomers includes EPDM (ethylene-propylene-diene terpolymer), isoprene, polyurethanes, silicones, and thermoplastic elastomers (TPE) such as styrenic block copolymers (SBC), thermoplastic olefins (TPO), and copolyesters (COPE). Examples of TPE trade names include Kraton®, Dynaflex®, Versaflex®, Versalloy® and Versollan™ from Dynaflex Corp., Grand Rapids, Mich.

Figure 9:
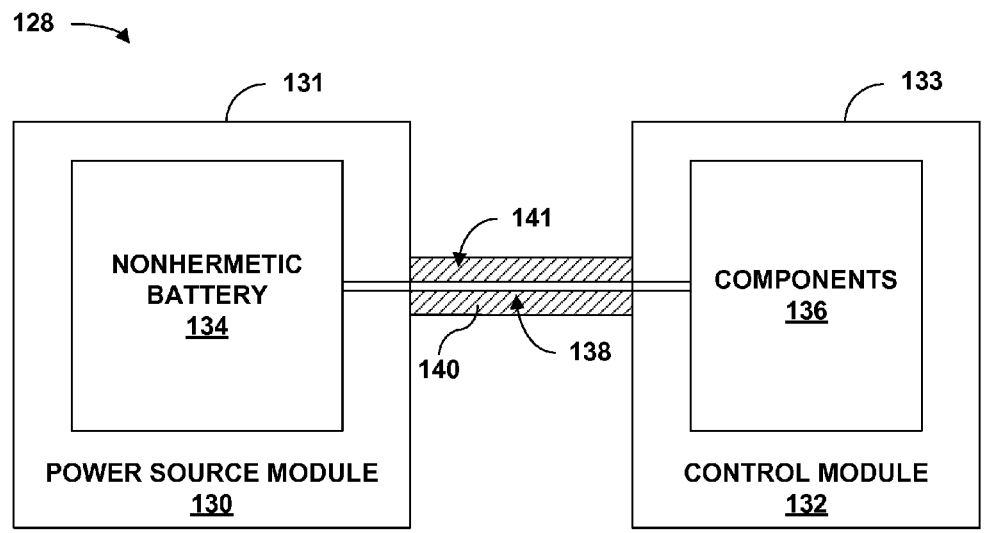

FIG. 9 is a block diagram illustrating a top view of an example IMD 128. IMD 128 includes a power source module 130 that includes a power source module housing 131 and a nonhermetic battery 134 within power source module housing 131. Additionally, IMD 128 further includes a control module 132 that includes a control module housing 133 and components 136 within control module housing 133. An electrical conductor 138 extends from nonhermetic battery 134 to components 136 and delivers power from nonhermetic battery 134 to components 136. Power source module 130 and control module 132 are coupled via an interconnect member 140, through which conductor 138 extends. Interconnect member 140 may define a void through which electrical conductor 138 extends.

The void of interconnect member 140 is filled with a material 141 to substantially impede movement of substances from nonhermetic battery 134 to components 136. In some embodiments, the interconnect member void is only partially filled with material 141. Material 141 may be one of backfilled, flowed, and inserted into the void of interconnect member 140. In the case where material 141 is inserted into the void, material 141 may be manipulated after insertion to create a substantially permanent air-tight seal with interconnect member 141. Material 141 is substantially impermeable to the substances from nonhermetic battery 134. Therefore, material 141 blocks corrosive compounds within the substances from reaching components 136 and potentially damaging IMD 128 and injuring a patient in which IMD 128 is implanted. Material 141 may also be flexible to allow interconnect member 140 to bend and flex, as described above.

A suitable material 141 may include a thermoplastic polymer such as polyolefin or ethylvinyl acetate. Material 141 may also comprise a thermosetting resin introduced to interconnect member 140 in a liquid or molten state and cured after filling. Examples of thermosetting resins include epoxies, silicones, polyurethanes, and isocyanates. It is advantageous to have material 141 comprise a material that expands, or at least minimally contracts, upon solidification. In that case, another example of material 141 may comprise a closed-cell foam that forms a gas upon curing such as isocyanate-terminated polyurethanes and acrylic latex polymers. Isocyanates, which have the property of forming strong bonds to metals such as aluminum, are therefore useful for forming a tight, permanent seal within interconnect member 140.

Material 141 may also include fillers that may be in a finely divided form such as flakes or powders. Fillers may either impart low permeability or absorption of the substances from nonhermetic battery 134. Absorbents may include getters described in more detail below. Materials with low permeability may include minerals, e.g., mica, ceramics, metals, and polymers. Material 141 may comprise a nonconductive metal, such as aluminum. If material 141 includes metals that would render material 141 electrically conductive, then nonhermetic battery 134 may require a complete or partial layer of electrical insulation from material 141. The electrical insulation may be a paint, a conformal coating, a potting compound, a polymer film, a ceramic, an oxide, or a passivation layer.

Figure 10:
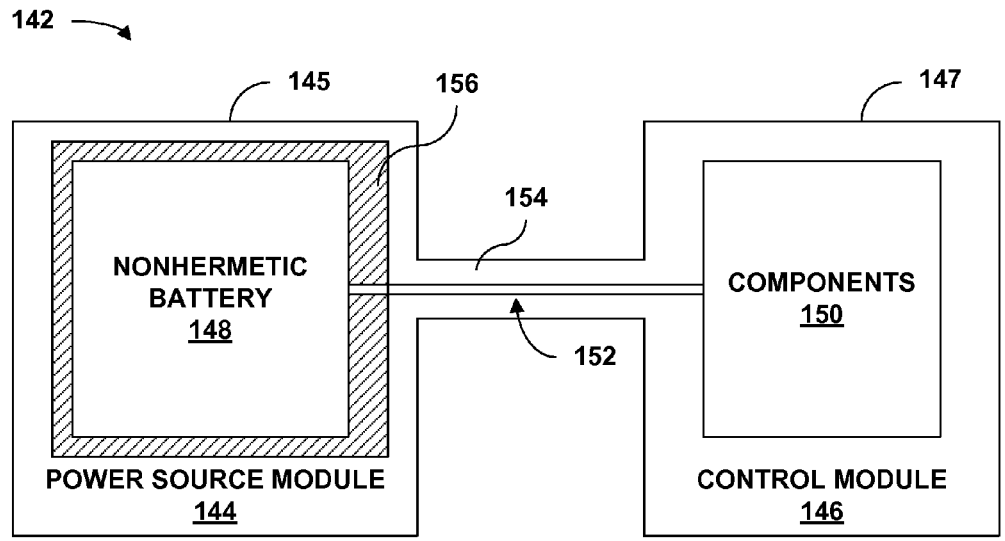

FIG. 10 is a block diagram illustrating a top view of an example IMD 142. IMD 142 includes a power source module 144 that includes a power source module housing 145 and a nonhermetic battery 148 within power source module housing 145. Additionally, IMD 142 further includes a control module 146 that includes a control module housing 147 and components 150 within control module housing 147. An electrical conductor 152 extends from nonhermetic battery 148 to components 150 and delivers power from nonhermetic battery 148 to components 150. Power source module 144 and control module 146 are coupled via an interconnect member 154, through which conductor 152 extends.

Power source control module 144 includes a material 156 that substantially encapsulates nonhermetic battery 148 within power source module housing 145. In some embodiments, material 156 may only partially encapsulate nonhermetic battery 148. Encapsulating nonhermetic battery 148 within material 156 substantially blocks movement of substances from leaving power source module housing 145. Material 156 is impermeable by corrosive compounds included in the substances from nonhermetic battery 148. The substances typically move out of nonhermetic battery 148 along termination wires or joints between sections of a battery case (not shown) or between the battery case and a nonhermetic feedthrough. Specifically designing material 156 to be resistant to the movement of substances from nonhermetic battery 148 at those locations increases containment of the corrosive compounds that may harm components 150 and a patient in which IMD 142 is implanted.

In some embodiments, nonhermetic battery 148 may be polymerized in place within power source module housing 145 with material 156. In that case, material 156 may comprise a thermosetting plastic, such as silicone, epoxy, or polyester. In other embodiments, material 145 may comprise a thermoplastic that, when melted, flows into power source module housing 145 to surround nonhermetic battery 148. In that case, material 145 may comprise a polyolefin, which includes polyethylene and polypropylene. In addition, material 145 may comprise one of the materials listed above for seal members 124 and 126 (FIG. 8) and material 141 (FIG. 9).

Figure 11:
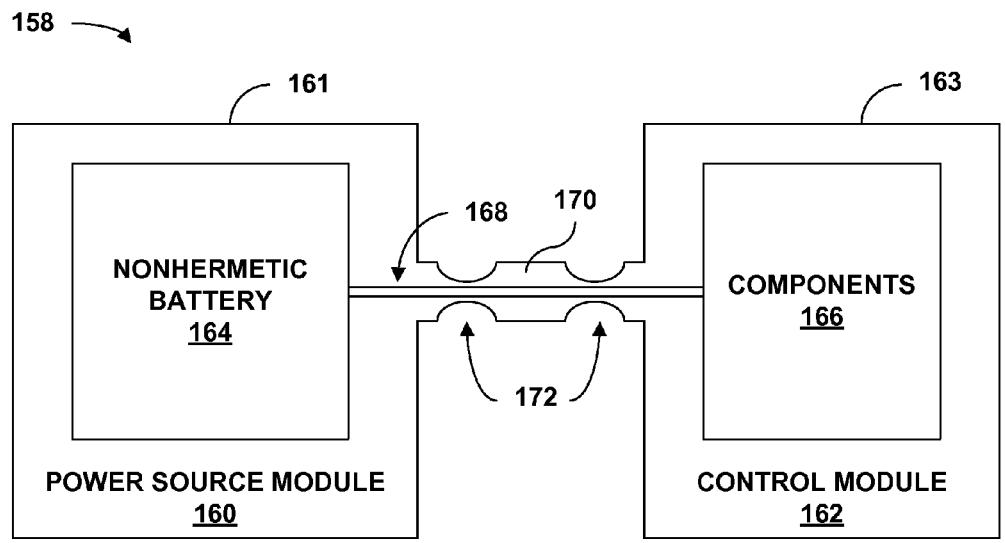

FIG. 11 is a block diagram illustrating a top view of an example IMD 158. IMD 158 includes a power source module 160 that includes a power source module housing 161 and a nonhermetic battery 164 within power source module housing 161. Additionally, IMD 158 further includes a control module 162 that includes a control module housing 163 and components 166 within control module housing 163. An electrical conductor 168 extends from nonhermetic battery 164 to components 166 and delivers power from nonhermetic battery 164 to components 166. Power source module 160 and control module 162 are coupled via an interconnect member 170, through which conductor 168 extends.

The movement of substances may be impeded by a length and/or cross-sectional area of interconnect member 170. A long interconnect member allows the substances from nonhermetic battery 164 to dissipate before reaching components 166. A small interconnect member cross-sectional area increases resistance against the movement to slow the diffusion rate of the substances from nonhermetic battery 164 to components 166. The ratio of interconnect member length to internal area should be kept as large as possible to increase diffusional resistance. In an embodiment where interconnect member 170 comprises a cylindrical shape, the ratio of interconnect member length to outside diameter is at least 10. As an example, an interconnect member length of 3 inches and an outside diameter of 0.05 inch gives a ratio of 60. The interconnect member ratio may also be applied to any of the IMDs described above.

As shown in FIG. 11, interconnect member 170 is crimped to create reduced-area regions 172 that substantially impede movement of substances from nonhermetic battery 164 to components 166. Crimping interconnect member 170 may involve pinching, rolling, drawing, or a combination thereof. In other embodiments, a plurality of reduced-area regions may be created along the length of interconnect member 170.

In some embodiments, a void defined by interconnect member 170 is at least partially filled with a material, substantially similar to FIG. 9. Reduced-cross-sectional area regions 172 are created after placing the material within the void of interconnect member 170. The material creates a pressure seal within interconnect member 170 at each reduced-cross-sectional area region 172. Refer to FIGS. 8 and 9 for a listing of materials that are only minimally permeable by substances from nonhermetic battery 164, and resistant to creep.

IMD 158 may also include a getter to substantially impede the movement of substances from nonhermetic battery 164 to components 166. The getter may be located within at least one of power source module 160, interconnect member 170, and control module 162. The getter absorbs or reacts with the substances within IMD 158 to form a solid nonvaporizable material or to substantially eliminate the corrosive compounds and/or elements that create corrosive compounds included in the substances from nonhermetic battery 164. In some embodiments, several getters are included in IMD 158. The getter may also be included within any of the IMDs described above.

The getter may comprise a desiccant, or any other type of getter for water. Common types of desiccants are silica gel or calcium carbonate, silico-aluminate, clay (montmorillonite), and molecular sieve. If $PF_6$ leaks out of nonhermetic battery 164 and water is available, the compounds will react to produce hydrofluoric acid (HF). However, if no water is available, no HF can be created. If any HF were to come in contact with components 166, it would damage components 166 and potentially injure a patient in which IMD 158 is implanted.

The getter may also comprise a getter for HF, such as fumed or gelled silica because silica is an excellent HF getter. The getter may further comprise a getter for organics. For example, the organic getter may be a type of carbon such as activated charcoal. Carbon has the ability to be formed and pressed into a specific shape, which allows the organic getter to fit in a variety of positions within IMD 158.

The getter may be located anywhere within the volume of IMD 158. Further, the getter may be randomly placed in IMD 158 between nonhermetic battery 164 and components 166. The getter may also be directly incorporated within a material to form elements such as seal members, material to fill interconnect member 170, material to encapsulate nonhermetic battery 164, or the like. For example, Multisorb Incorporated of Buffalo, N.Y., USA manufactures desiccants in forms that may incorporate easily within IMD 158, including machinable material, hot-melt glue, and plastic films.

In addition, nonhermetic battery 164 may include a gel, polymer, or solid electrolyte instead of a gas or liquid electrolyte. The gel, polymer, or solid electrolyte acts as a barrier within nonhermetic battery 164 by substantially eliminating movement of substances from nonhermetic battery 164. The gel, polymer, or solid electrolyte reduces vapor pressure within nonhermetic battery 164, which reduces a chance of nonhermetic battery 164 leaking. Furthermore, if nonhermetic battery 164 does leak, the gel, polymer, or solid electrolyte has a much smaller chance of leaving nonhermetic battery 164 than a gas or fluid electrolyte. An electrolyte gelling agent such as polyvinylidene fluoride (PVDF), polyvinylidene fluoride-hexafluoropropylene (PVDF-HFP) copolymer, polyethylene oxide (PEO), silicon, or a mixture thereof, is used to create the gelled electrolyte. The polymer or solid electrolyte may create a thin-film nonhermetic battery. The solid electrolyte may comprise ceramic or glass. The nonhermetic batteries included in the IMDs described above may also include the gel, polymer, or solid electrolyte.

In some embodiments, IMD 158 may not include power source module housing 160. In that case, nonhermetic battery 164 may couple directly to interconnect member 170 by a hermetic weld or braise around the connection area. Sealing the interface area between nonhermetic battery 164 and interconnect member 170 substantially blocks the substances from entering the patient's body. Eliminating the power source module housing 160 allows IMD 158 to comprise a further reduced profile thickness. The IMDs described above may also not include a power source module housing that fully encapsulates the nonhermetic battery.

Figure 12:
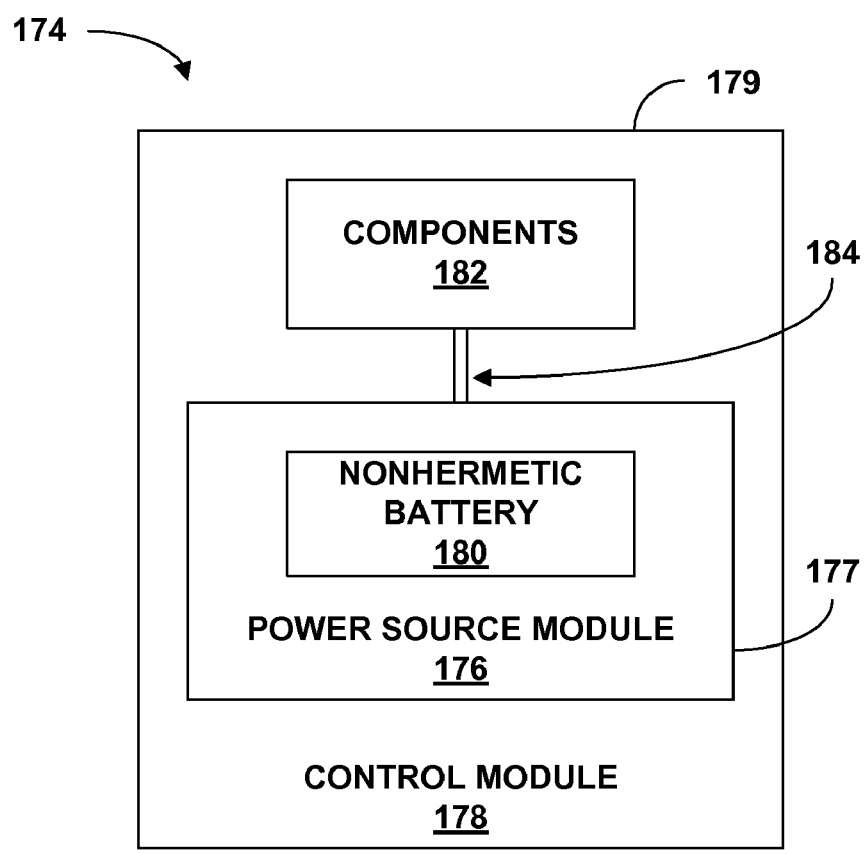
FIG. 12 is a block diagram illustrating a top view of another example IMD.

FIG. 12 is a block diagram illustrating a top view of another example IMD 174. IMD 174 includes a power source module 176 that includes a power source module housing 177 and a nonhermetic battery 180 within power source module housing 177. Control module 178 includes a control module housing 179 and components 182 within control module housing 179. Power source module 176 is included within control module housing 179. An electrical conductor 184 extends from nonhermetic battery 180 to components 182 and delivers power from nonhermetic battery 180 to components 178. In some embodiments, components 182 may comprise control electronics.

IMD 174 illustrates an IMD set-up as an alternative to the IMDs illustrated in FIGS. 6-11. The illustrated embodiment may correspond to a non-modular IMD. For example, IMD 174 may comprise a conventional IMD with a single housing that houses substantially all of the IMD's components. The barriers described above may also be applied to IMD 174 to block, absorb and/or dissipate the movement of substances between nonhermetic battery 180 and components 182.

Various embodiments of the invention have been described. For example, an implantable medical device (IMD) including a nonhermetic battery has been described. The nonhermetic battery reduces a profile and a manufacturing cost of the IMD. The IMD also includes a barrier to impede movement of substances from the nonhermetic battery from reaching components within the IMD and injuring a patient in which the IMD is implanted. A variety of barriers are described including hermetic feedthroughs, seal members, material to encapsulate the nonhermetic battery, chemical getters, and gel, polymer, or solid electrolytes. A modular IMD is also described that includes an interconnect member to couple a module including the nonhermetic battery to a module including the components. Barriers may also be including in the interconnect member, such as length, cross-sectional area, and material filling at least a portion of a void defined by the interconnect member.

Nevertheless, various modifications may be made without departing from the scope of the invention. For example, the IMD described above may include any nonhermetic electrochemical generator, such as a fuel cell, instead of a nonhermetic battery. A fuel cell is designed to vent the substances created by operation. The barriers provided by the invention enable a fuel cell or similar generator to be included in an IMD as the barriers substantially impede the movement of substances. Furthermore, the components with the IMD may refer to control electronics as well as sensor control components and other control mechanisms that may or may not be included within the control module housing.

These and other embodiments are within the scope of the following claims.

The invention claimed is:

1. A method of manufacturing an implantable medical device, the method comprising:
   forming a control module including components;
   forming a control module housing to house the components;
   forming a power source module including a nonhermetic battery and power management circuitry;
   forming a power source module housing to house the nonhermetic battery and the power management circuitry, wherein the nonhermetic battery is not enclosed in a hermetic housing within the power source module; and
   forming an interconnect member to couple the control module and the power source module, the interconnect member including an electrical conductor that extends through the interconnect member to deliver power from the nonhermetic battery to the components.

2. The method of claim 1, further comprising housing the nonhermetic battery within a nonhermetic housing included in the power source module housing.

3. The method of claim 1, Further comprising forming a barrier between the components and the nonhermetic battery that substantially impedes movement of substances from the nonhermetic battery to the components.

4. The method of claim 3, wherein the barrier comprises a hermetic feedthrough.

5. The method of claim 3, wherein the barrier comprises a length and cross-sectional area of the interconnect member.

6. The method of claim 3, wherein the barrier comprises a seal member positioned within the interconnect member.

7. The method of claim 3, wherein forming the interconnect member includes defining a void through which the electrical conductor extends, wherein the barrier comprises a material that tells at least a portion of the interconnect member void.

8. The method of claim 3, wherein the barrier comprises a material that substantially encapsulates at least a portion of the nonhermetic battery within the power source module housing.

9. The method of claim 3, wherein the barrier comprises a getter within at least one of the power source module housing, the interconnect member or the control module housing.

10. The method of claim 3, wherein the barrier comprises one of a gel, a polymer, or a solid electrolyte within the nonhermetic battery.

11. The method of claim 1, further comprising forming a feedthrough, through which the electrical conductor extends, as a part of the power source module housing.

12. The method of claim 11, wherein forming the power source module housing includes forming an interlace area of the power source module housing with the interconnect member that comprises a thickness at least as thick as an outside cross-sectional area of the feedthrough.

13. The method of claim 1, further comprising forming a feedthrough, through which the electrical conductor extends, as a part of the control module housing.

14. The method of claim 13, wherein forming the interconnect member includes forming an interface area of the interconnect member with the control module housing that comprises a thickness at least as thick as an outside cross-sectional area of the feedthrough.

15. The method of claim 1, further comprising forming the power source module housing and the interconnect member to comprise thicknesses less than an outside cross-sectional area of a feedthrough through which the electrical conductor extends.

16. The method of claim 1, wherein the components comprise control electronics.

17. A method of manufacturing an implantable medical device, the method comprising:

forming a control module including components;

forming a control module housing to house the components;

forming a power source module including a nonhermetic battery and power management circuitry;

forming a power source module housing to house the nonhermetic battery and the power management circuitry, the nonhermetic battery is not enclosed in a hermetic housing within the power source module;

forming an interconnect member to couple the control module housing and the power source module housing; and forming a barrier between the components and the nonhermetic battery that is separate from any housing and that substantially impedes movement of substances from the nonhermetic battery through the interconnect member to the components.

18. The method of claim 17, wherein the interconnect member includes an electrical conductor that delivers power from the nonhermetic battery to the components.

19. The method of claim 17, wherein the barrier comprises a seal member positioned within the interconnect member.

20. The method of claim 17, wherein the barrier comprises a material that substantially encapsulates at least a portion of the nonhermetic battery within the power source module housing.

* * * * *